United States Patent

Yokoo et al.

Patent Number: 5,712,263
Date of Patent: Jan. 27, 1998

[54] STEROID DERIVATIVES

[75] Inventors: Chihiro Yokoo; Hisaya Wada; Hidemichi Mitome; Tatsuhiko Sano; Katsuo Hatayama; Yasuji Yamada, all of Tokyo, Japan

[73] Assignee: Taisho Pharmaceutical Co., Ltd., Tokyo, Japan

[21] Appl. No.: 663,929

[22] Filed: Jun. 14, 1996

Related U.S. Application Data

[63] Continuation of PCT/JP94/02102 Dec. 14, 1994.

[30] Foreign Application Priority Data

Dec. 15, 1993 [JP] Japan .................. 5-315246

[51] Int. Cl.$^6$ .............. A61K 31/58; C07J 17/00
[52] U.S. Cl. ............................. 514/172; 540/94
[58] Field of Search ..................... 514/172; 540/94

[56] References Cited

U.S. PATENT DOCUMENTS 5,122,521   6/1992   Yamada .

FOREIGN PATENT DOCUMENTS 467 664   1/1992   European Pat. Off. .

OTHER PUBLICATIONS

Tschesche, R. and Schwinum, E., "Synthese von 12α.20R–Epoxy–5α.14β.17βH–pregnanen", *Chem. Ber* 100:464–479 (1967).

Elwood, et al, *Biochemistry*, 36(6), 1997, pp. 1467–1478.

Iguchi, et al: "Aragusterol A: A Potent Antitumor Marine Steroid from the Okinawan Sponge of the Genus", Xestospongia, *Tetrahedron Letters*, vol. 34, No. 39, pp. 6277–6280, 1993.

Tennen Yuki Kagobutsu Toronkai koen Yoshishu 35th,p. 274–281 (1993) Iguchi, et al:"Aragusterol A, B and C: potent antitumor marine steroids from the Okinawa sponge of the genis Xestospongia" (Chemical Abstracts 121:99238).

*Primary Examiner*—Kimberly J. Prior
*Attorney, Agent, or Firm*—Cushman Darby & Cushman IP Group of Pillsbury Madison & Sutro LLP

[57] ABSTRACT

To provide novel steroid derivatives having an antitumor action which can be synthesized efficiently and stereoselectively by means of synthetic organic chemistry. A steroid derivative represented by the formula:

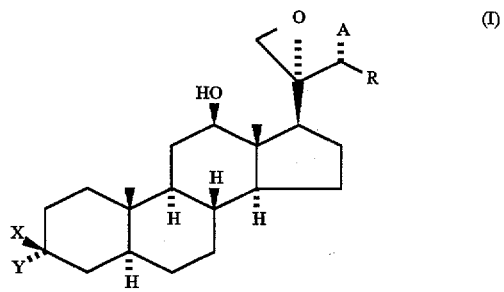

wherein R is an alkyl group having 1 to 13 carbon atoms, A is a hydroxyl group or a group easily hydrolyzable to a hydroxyl group, X and Y together form an oxo group or an alkylenedioxy group having 2 or 3 carbon atoms, X is a hydroxyl group, an alkoxy group having 1 to 5 carbon atoms or a group easily hydrolyzable to a hydroxyl group, Y is a hydrogen atom or an alkoxy group having 1 to 5 carbon atoms, with the proviso that when X is a hydroxyl group or a group easily hydrolyzable to a hydroxyl group, Y is a hydrogen atom, and when X is an alkoxy group having 1 to 5 carbon atoms, Y is an alkoxy group having 1 to 5 carbon atoms, or a salt thereof.

4 Claims, No Drawings

STEROID DERIVATIVES

This is a Continuation of International Application No. PCT/JP94/02102 filed Dec. 14, 1994 which designated the U.S.

TECHNICAL FIELD

The present invention relates to novel steroid derivatives having an antitumor action.

BACKGROUND ART

A compound isolated from sponges of the genus Xestospongia which is described in US Pat. No. 5,122,521 (hereinafter referred to as "Compound A") has been known as a compound similar in structure to compounds of the present invention. Compound A has an excellent antitumor action, and therefore is expected as a novel antitumor agent. However, as being an originally natural compound in ocean, it was difficult to constantly supply Compound A on a large scale due to a problem of maintaining the resource. In addition, an efficiently stereoselective synthesis of Compound A was very difficult, because Compound A has 5 asymmetric carbon atoms in the side chain at the 17-position.

An object of the present invention is to provide novel steroid compounds having an antitumor action which can be synthesized by means of synthetic organic chemistry.

DISCLOSURE OF THE INVENTION

As a result of extensive researches about simplification of the side chain at the 17-position of Compound A, the present inventors synthesized novel steroid derivatives having the number of asymmetric carbon atoms reduced to 2 in the side chain at the 17-position, and found that these compounds have a comparable antitumor effect to Compound A, thereby the present invention has been accomplished.

The present invention is illustrated as follows.

The present invention is a steroid derivative represented by Formula (I):

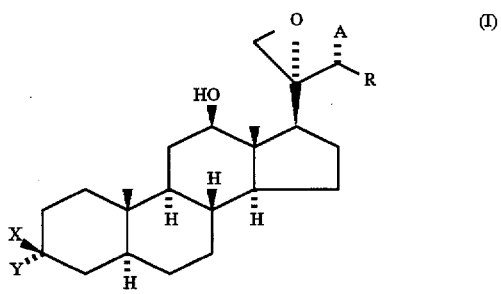

wherein R is a straight or branched alkyl group having 1 to 13 carbon atoms, A is a hydroxyl group or a group easily hydrolyzable to a hydroxyl group, X and Y together form an oxo group or an alkylenedioxy group having 2 or 3 carbon atoms, X is a hydroxyl group, an alkoxy group having 1 to 5 carbon atoms or a group easily hydrolyzable to a hydroxyl group, Y is a hydrogen atom or an alkoxy group having 1 to 5 carbon atoms, with the proviso that when X is a hydroxyl group or a group easily hydrolyzable to a hydroxyl group, Y is a hydrogen atom, and when X is an alkoxy group having 1 to 5 carbon atoms, Y is an alkoxy group having 1 to 5 carbon atoms, or a salt thereof.

In the present invention, the alkyl group refers to a straight or branched alkyl group such as, for example, a methyl group, an ethyl group, a propyl group, an isopropyl group, a butyl group, an isobutyl group, a pentyl group, an isopentyl group, a hexyl group, an isohexyl group, a heptyl group, an isoheptyl group, an octyl group, an isooctyl group, a nonyl group, an isononyl group, a decyl group, an isodecyl group, a dodecyl group, an isododecyl group, a tridecyl group or an isotridecyl group, and preferably an isobutyl group, an isopentyl group, an isohexyl group, an isoheptyl group or an isooctyl group. The alkoxy group refers to a straight or branched alkoxy group such as, for example, a methoxy group, an ethoxy group, a propoxy group, an isopropoxy group, a butoxy group, an isobutoxy group, a pentoxy group or an isopentoxy group, and preferably a methoxy group or an ethoxy group.

The group easily hydrolyzable to a hydroxyl group refers to a group easily hydrolyzable to a hydroxyl group by a conventional hydrolysis with an acid or an alkali, which exemplifies, a substituted alkanoyloxy group, a sulfoxy group, a phosphonoxy group or a phosphinoxy group. Examples of the substituted alkanoyloxy group are an N,N-dimethylglycyloxy group, an N,N-diethylglycyloxy group, a 3-(N,N-dimethylamino)-propionyloxy group, a 3-(N,N-diethylamino)propionyloxy group, a 4-(N,N-dimethylamino)butyryloxy group, a succinyloxy group, a glutaryloxy group and a 3-sulfopropionyloxy group. Preferable examples of the group easily hydrolyzable to a hydroxyl group are an N,N-dimethylglycyloxy group, an N,N-diethylglycyloxy group, a succinyloxy group and a 3-sulfopropionyloxy group.

The salt in the present invention refers to a pharmaceutically acceptable salt such as, for example, salts with inorganic acids (e.g. hydrochloric acid, hydrobromic acid, hydroiodic acid, sulfuric acid, nitric acid or phosphoric acid), salts with organic acids (e.g. formic acid, acetic acid, propionic acid, lactic acid, tartaric acid, fumaric acid, maleic acid, succinic acid, ascorbic acid, malic acid, salicylic acid, trifluoroacetic acid, methanesulfonic acid or p-toluenesulfonic acid), salts with alkali metals (e.g. sodium or potassium), salts with alkali earth metals (e.g. magnesium or calcium), salts with alkylamines (e.g. triethylamine) or ammonium salt.

The compounds of Formula (I) of the present invention can be synthesized using a steroid derivative 3β, 12β-dihydroxy-5α-pregnan-20-one (1) described in the literature (Chem. Ber. 100, 464, 1967) as a starting material according to the preparation methods shown in the following Schemes 1, 2 and 3. The preparation methods of the compounds of the present invention can be illustrated as follows.

Firstly, the preparation methods of the compounds of the present invention which are obtained by the synthesis methods shown in Schemes 1 and 2 are illustrated.

Scheme 1

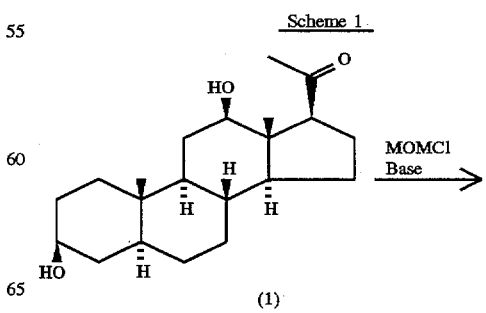

-continued
Scheme 1
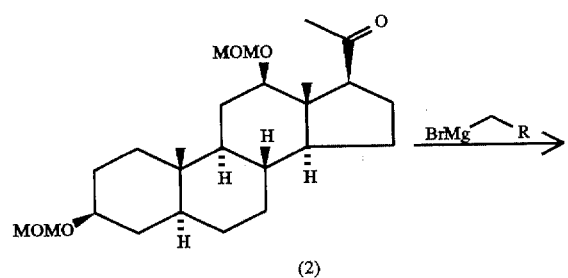
(2)
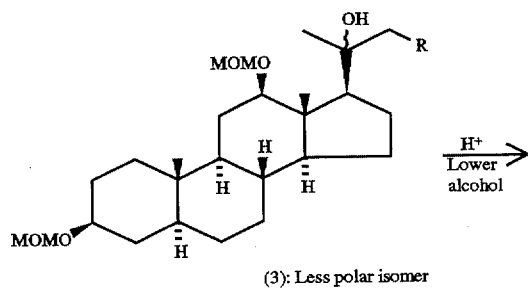
(3): Less polar isomer (main product)
(4): More polar isomer
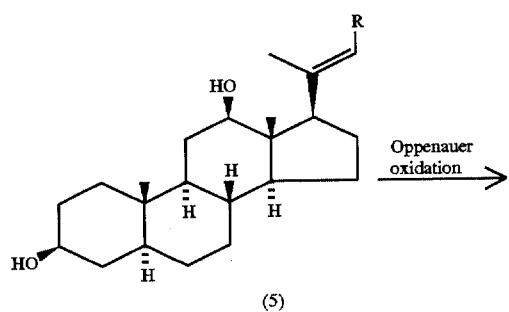
(5)
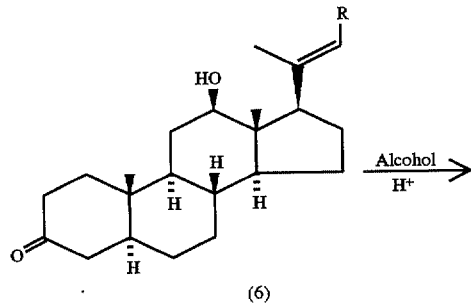
(6)
-continued
Scheme 1
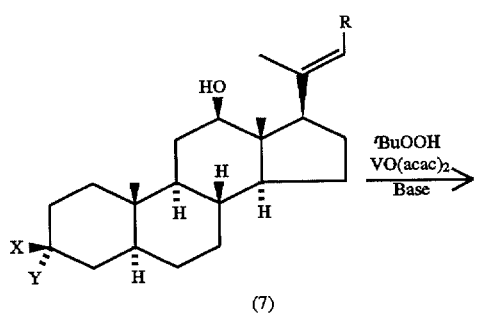
(7)
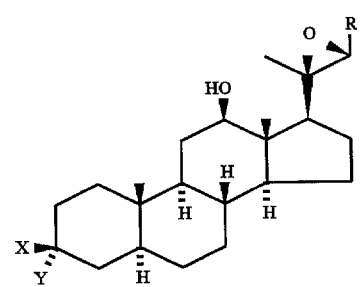
(8): More polar isomer (main product)
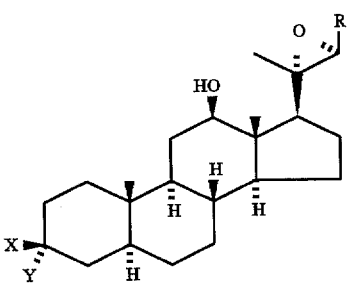
MOM: methoxymethyl
acac: acetylacetonate
(9): Less polar isomer

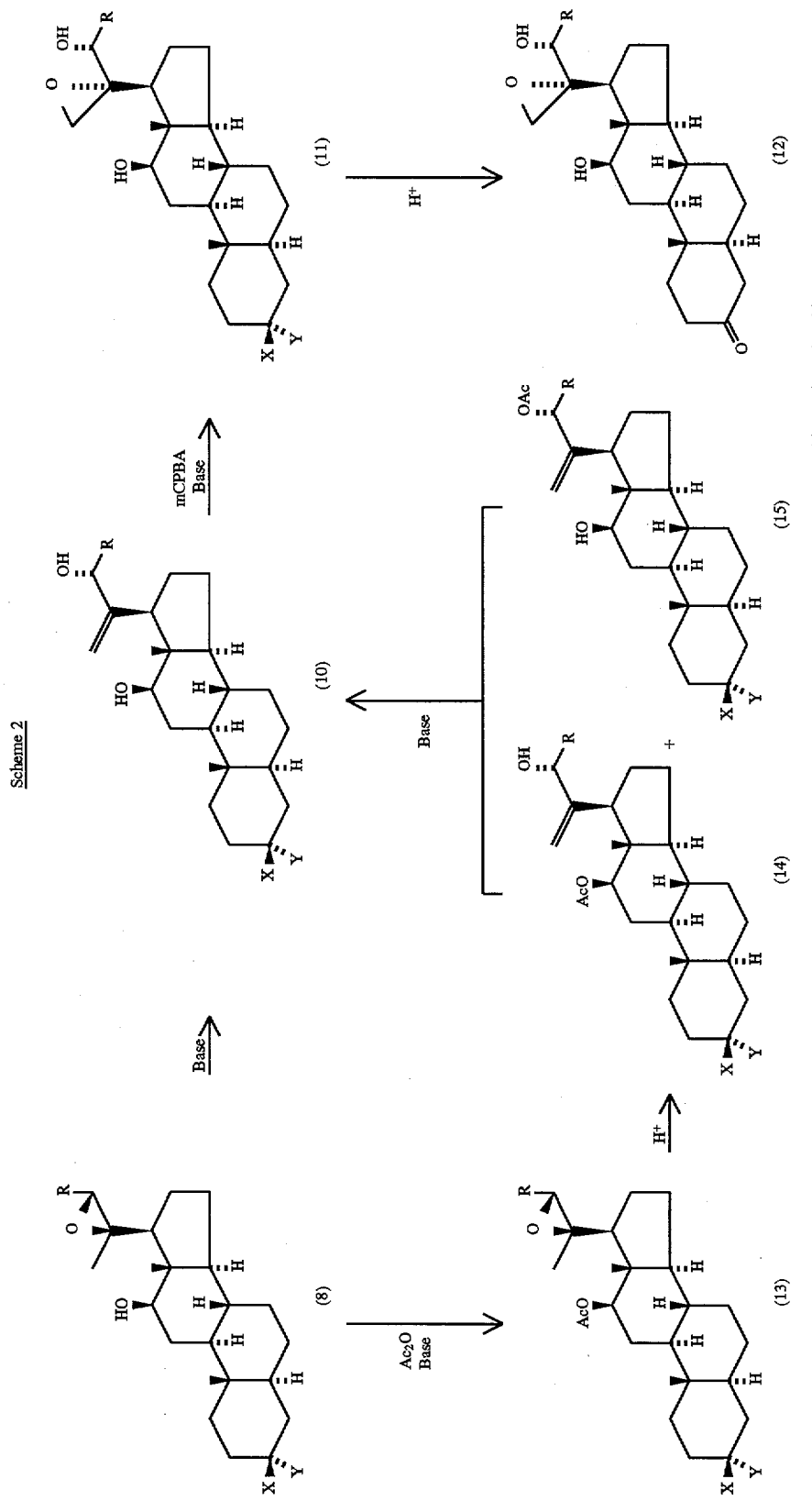

Compound (1) is reacted with methoxymethyl chloride in the presence of a base such as diisopropylethylamine to give a derivative (2) wherein hydroxyl groups at the 3- and 12-positions are protected. Subsequently, Compound (2) is reacted with a Grignard's reagent to give alcohol derivatives, each having a hydroxyl group at the 20-position, which include a less polar isomer thereof (3) and a more polar isomer thereof (4). A mixture of Compounds (3) and (4) is reacted with an acid such as conc. hydrochloric acid in a lower alcohol such as isopropanol to give a 20,22-(E)-olefin derivative (5) as a main product. Compound (5) is subjected to an Oppenauer oxidation to give a ketone derivative (6) having a ketone group at the 3-position, which is then reacted with an alcohol having 1 to 5 carbon atoms such as ethylene glycol or propylene glycol in the presence of an acid catalyst such as p-toluenesulfonic acid to give a protected ketone derivative (7) having a protected ketone group at the 3-position. Compound (7) is reacted with tert-butyl hydroperoxide in the presence of a vanadium catalyst and in the absence or presence of a base such as sodium bicarbonate to give 20,22-β-epoxy derivative (8), i.e. a more polar isomer thereof and 20,22-α-epoxy derivative (9), i.e. a less polar isomer thereof at the yield ratio of about 16:1–5:1. Compound (8) is reacted with a base such as aluminum tert-butoxide, lithium diisopropylamide or bromomagnesium diisopropylamide to give an allyl alcohol derivative (10), which is then reacted with m-chloroperbenzoic acid in the presence of a base such as sodium bicarbonate to give an epoxy alcohol derivative (11) which is the compound of the present invention.

In addition, Compound (11) is treated with an acid such as acetic acid to give an epoxy alcohol derivative (12) having a ketone group at the 3-position, which is the compound of the present invention.

The allyl alcohol derivative (10) can be also obtained according to an alternative method. That is, Compound (8) is reacted with acetic anhydride in the presence of an organic base such as pyridine, and the resulting 12β-acetoxy-20,22-β-epoxy derivative (13) is reacted with an acid such as hydrogen chloride in an organic solvent to give a mixture of a 12β-acetoxy-allyl alcohol derivative (14) and a 22α-acetoxy derivative (15), which are then hydrolyzed using a base such as potassium carbonate to give an allyl alcohol derivative (10).

Then, the preparation methods of the compounds of the present invention obtained according to the synthesis methods shown in Scheme 3 are illustrated.

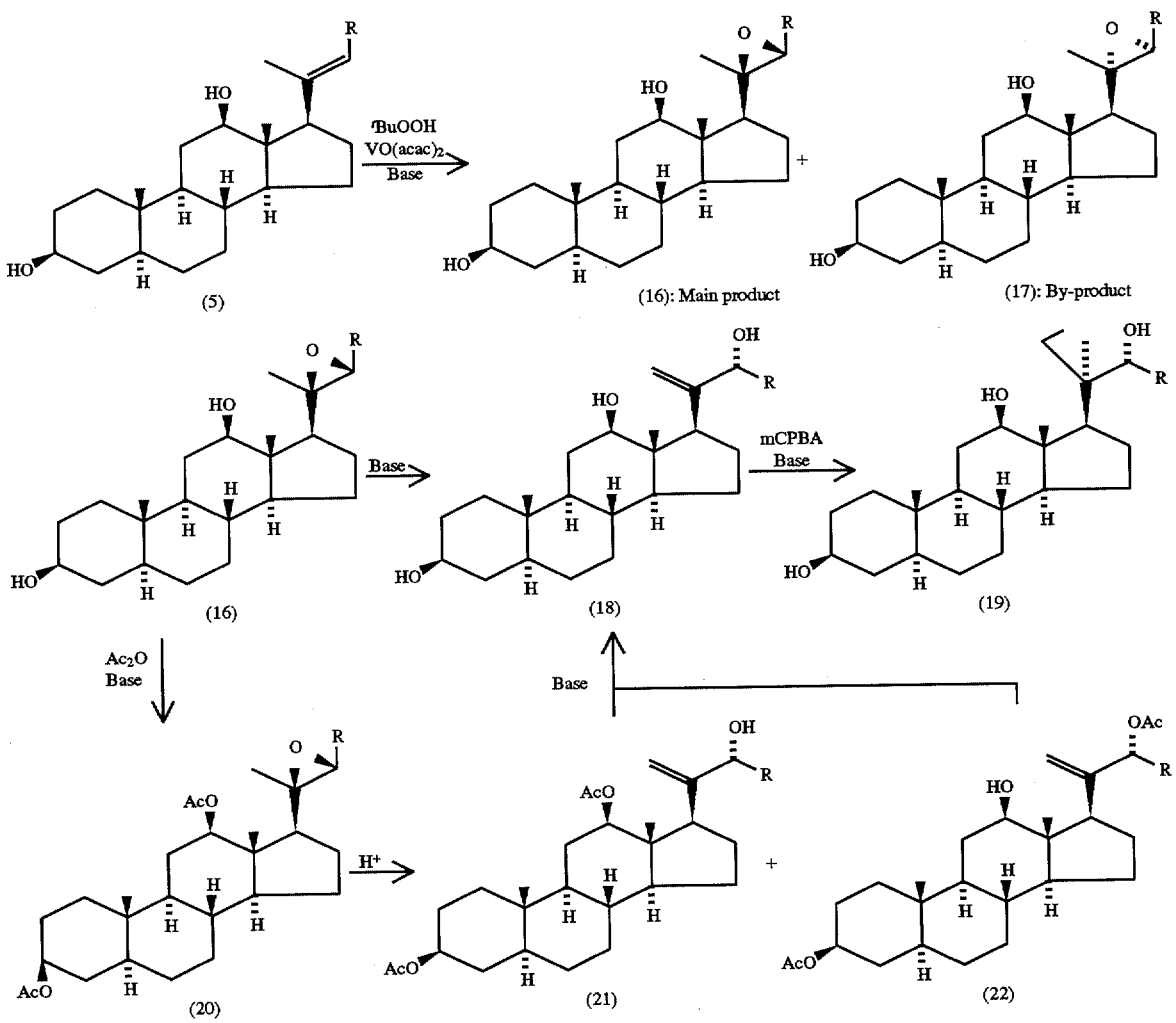

Firstly, the 3β, 12β-dihydroxy-20,22-(E)-olefin derivative (5) obtained by the preparation method shown in Scheme 1 is reacted with tert-butyl hydroperoxide in the presence of a vanadium catalyst and in the absence or presence of a base such as sodium bicarbonate to give a 20,22-β-epoxy derivative (16) as a main product and a 20,22-α-epoxy derivative (17) as a by-product at the yield ratio of about 10:1. Next, Compound (16) is reacted with a base such as aluminum tert-butoxide, lithium diisopropylamide or bromomagnesium diisopropylamide to give an allyl alcohol derivative (18), which is then reacted with m-chloroperbenzoic acid in the absence or presence of a base such as sodium bicarbonate to give a 3β, 12β-dihydroxy-epoxy alcohol derivative (19) which is the compound of the present invention.

The allyl alcohol derivative (18) can be also obtained via 3β, 12β-diacetoxy derivatives (20) and (21) and a 3β, 22α-diacetoxy derivative (22) according to an alternative method shown in Scheme 2.

Next, the preparation methods of the compounds of the present invention having a group easily hydrolyzable to a hydroxyl group are illustrated as follows: These compounds can be prepared from Compound (11), (12) or (19) shown in Schemes as a starting material.

Firstly, the compound wherein the group easily hydrolyzable to a hydroxyl group is a substituted alkanoyloxy group can be prepared by reacting Compound (11), (12) or (19) with a corresponding substituted alkane acid, an acid halide thereof or an acid anhydride thereof under the conditions of a conventional esterification. The compound wherein the substituted alkanoyloxy group is a 3-sulfopropionyloxy group can be prepared by reacting Compound (11), (12) or (19) with acrylic acid or acryloyl chloride under the conditions of a conventional esterification, and then reacting the resulting acrylate ester with sodium pyrosulfite.

The compound wherein the group easily hydrolyzable to a hydroxyl group is a sulfoxy group (sulfuric acid monoester) can be prepared by reacting Compound (11), (12) or (19) with sulfur trioxide pyridine complex.

The compound wherein the group easily hydrolyzable to a hydroxyl group is a phosphonoxy group (phosphoric acid monoester) can be prepared by reacting Compound (11), (12) or (19) under the conditions of a conventional phosphoric acid esterification, and then deprotecting the resulting protected phosphoric acid triester. Alternatively, this compound can be also prepared by reacting Compound (11), (12) or (19) under the conditions of a conventional phosphorous acid esterification, oxidizing the resulting protected phosphorous acid triester in a conventional manner, and then deprotecting the resulting protected phosphoric acid triester.

The compound wherein the group easily hydrolyzable to a hydroxyl group is a phosphinoxy group (phosphorous acid monoester) can be prepared by reacting Compound (11), (12) or (19) under the conditions of a conventional phosphorous acid monoesterification.

Of the compounds of the present invention, a salt-formable compounds can be converted into a corresponding salt under a conventional treatment.

For the use as medicines, the steroid compound or salt thereof of the present invention is mixed with conventional pharmaceutically acceptable carriers (e.g. talc, gum arabic, lactose, magnesium stearate or corn starch) to give oral or parenteral dosage forms, examples of which are tablets, granules, powders, capsules, syrups, suspensions and injections. The dosage for the treatment of adult human is 1 to 500 mg per day, in 2 or 3 divided doses, and can be varied depending on the age, body weight and symptoms of the patient.

BEST MODE FOR CARRYING OUT THE INVENTION

The present invention is illustrated in more detail by the following examples. In the symbols which are followed by the number of the compound described in the examples, "a" means the compounds wherein R is an isobutyl group in Schemes 1, 2 and 3, "b" means the compounds wherein R is an isopentyl group in Schemes 1 and 2, "c" means the compounds wherein R is a methyl group in Schemes 1 and 2, and "d" means the compounds wherein R is a tridecyl group in Schemes 1 and 2.

EXAMPLE 1

(cases of the compounds wherein R is an isobutyl group, and X and Y are connected together to form an ethylenedioxy group in Schemes 1 and 2)

(1) Synthesis of Compound (2)

7.0 g of Compound (1) was dissolved in 70 ml of methylene chloride, and then 5.05 g of methoxymethyl chloride and 8.10 g of diisopropylethylamine were added thereto, followed by reflux for 7 hours. The reaction solution was allowed to stand for cooling, and then ice water was added thereto, followed by extraction with ethyl acetate. The extract was successively washed with water and a saturated aqueous sodium chloride solution and dried over anhydrous magnesium sulfate. The solvent was evaporated, and the resulting crude product was subjected to silica gel column chromatography eluting with hexane:ethyl acetate=2:1 (v/v) to give fractions of Compound (2). After evaporation of the solvent, recrystallization from hexane gave 6.7 g (yield: 76%) of colorless prisms (2).

mp: 94°–95° C.

Anal. Calcd for $C_{25}H_{42}O_5$: C, 71.05; H, 10.02

Found; C, 71.25; H, 10.10

IR (KBr) $cm^{-1}$: 1701, 1150, 1042

$^1$H-NMR (CDCl$_3$) δ (ppm):

0.74 (3H, s), 0.82 (3H, s), 2.19 (3H, s), 2.68 (1H, t, J=8 Hz), 3.34 (3H, s), 3.36 (3H, s), 3.34–3.43 (1H, m), 3.43–3.58 (1H, m), 4.63–4.74 (4H, m)

FABMS (+KI) m/z: 461 (MK$^+$)

(2) Syntheses of Compound (3a) and Compound (4a)

A solution of 10.72 g of isoamyl bromide in 100 ml of diethyl ether was added dropwise to 2.01 g of magnesium under an argon atmosphere at room temperature, followed by stirring for 30 minutes. The reaction solution was cooled to 3° C., and then a solution of 10.0 g of Compound (2) in 100 ml of benzene was added thereto at 5° C. or below, followed by stirring at 3° C. for 3 hours. The reaction solution was poured into an aqueous ammonium chloride solution and extracted with ethyl acetate. The extract was washed with a saturated aqueous sodium chloride solution and dried over anhydrous magnesium sulfate. After evaporation of the solvent, the resulting colorless oil was purified by silica gel column chromatography eluting with hexane-:ethyl acetate=3:1 (v/v), thereby 9.45 g (yield: 81%) of a colorless oil (3a) was obtained from earlier eluting fractions, and 1.57 g (yield: 13%) of a colorless oil (4a) was obtained from later eluting fractions.

Compound (3a)

IR (neat) $cm^{-1}$: 3430, 1152, 1050

$^1$H-NMR (CDCl$_3$) δ (ppm):

0.83 (3H, s), 0.85 (3H, s), 0.87 (3H, d, J=5 Hz), 0.88 (3H, d, J=5 Hz), 1.18 (3H, s), 3.31–3.59 (2H, m), 3.35 (3H, s), 3.41 (3H, s), 4.67 (2H, s), 4.70 (1H, d, J=6 Hz), 4.84 (1H, d, J=6 Hz), 5.15 (1H, br s)

FABMS (+KI) m/z: 533 (MK$^+$)

Compound (4a)

IR (neat) cm$^{-1}$: 3431, 1152, 1050

$^1$H-NMR (CDCl$_3$) δ (ppm):

0.82 (3H, s), 0.85 (3H, s), 0.87 (3H, d, J=6 Hz), 0.89 (3H, d, J=6 Hz), 1.03 (3H, s), 3.33–3.43 (1H, m), 3.36 (3H, s), 3.40 (3H, s), 3.42–3.58 (1H, m), 4.67 (2H, s), 4.70 (1H, d, J=6 Hz), 4.83 (1H, d, J=6 Hz)

FABMS (+KI) m/z: 533 (MK$^+$)

(3) Synthesis of Compound (5a)

A mixture of 9.45 g of Compound (3a) and 1.57 g of Compound (4a) was dissolved in 330 ml of isopropanol, and then 1.98 ml of conc. hydrochloric acid was added thereto, followed by reflux for 9 hours. After cooling the reaction solution, the solvent was evaporated, and resulting residue was dissolved in chloroform and washed with a saturated aqueous sodium chloride solution. The solution was dried over anhydrous magnesium sulfate, and the solvent was evaporated. The resulting crude product was subjected to silica gel column chromatography eluting with chloroform:ethyl acetate=10:1 (v/v) to give fractions of Compound (5a). After evaporation of the solvent, recrystallization from ethyl acetate gave 5.87 g (yield: 68%) of colorless fine needles (5a).

mp: 195°–198° C.

Anal. Calcd for C$_{26}$H$_{44}$O$_2$: C, 80.35; H, 11.41

Found: C, 80.64; H, 11.59

IR (KBr) cm$^{-1}$: 3460, 2949, 2925, 2867, 1466

$^1$H-NMR (CDCl$_3$) δ (ppm):

0.73 (3H, s), 0.81 (3H, s), 0.89 (6H, d, J=5 Hz), 1.67 (3H, s), 1.90 (2H, t, J=6 Hz), 2.29 (1H, t, J=8 Hz), 3.50–3.68 (2H, m), 5.51 (1H, t, J=6 Hz)

FABMS (+KI) m/z: 427 (MK$^+$)

(4) Synthesis of Compound (6a)

2.0 g of Compound (5a) was dissolved in 62 ml of toluene, and then 16 ml of cyclohexanone was added thereto, followed by reflux using a Dean stark trap for 10 minutes. Subsequently, 1.58 g of aluminum isopropoxide was added, and the mixture was refluxed for an hour. The reaction solution, after addition of dil. hydrochloric acid, was extracted with ethyl acetate, washed with a saturated aqueous sodium chloride solution and dried over anhydrous magnesium sulfate. After evaporation of the solvent, the resulting crude product was purified by silica gel column chromatography eluting with hexane:ethyl acetate=6:1 (v/v) to give 1.45 g (yield: 73%) of colorless fine needles (6a).

mp: 103°–105° C.

Anal. Calcd for C$_{26}$H$_{42}$O$_2$: C, 80.77; H, 10.95

Found: C, 80.65; H, 11.02

IR (KBr) cm$^{-1}$: 3555, 3420, 1719

$^1$H-NMR (CDCl$_3$) δ (ppm):

0.76 (3H, s), 0.86 (3H, d, J=5 Hz), 0.87 (3H, d, J=5 Hz), 1.02 (3H, s), 1.67 (3H, s), 3.61 (1H, dd, J=10 and 5 Hz), 5.52 (1H, dt, J=6 and 1 Hz)

FABMS (+KI) m/z: 425 (MK$^+$)

(5) Synthesis of Compound (7a)

1.8 g of Compound (6a) was dissolved in 90 ml of benzene, and then 2.6 ml of ethylene glycol and 0.08 g of p-toluenesulfonic acid were added thereto, followed by reflux using a Dean stark trap for 10 minutes. The reaction solution, after addition of ethyl acetate, was successively washed with a saturated aqueous sodium bicarbonate solution and a saturated aqueous sodium chloride solution and dried over anhydrous magnesium sulfate. After evaporation of the solvent, the resulting crude product was purified by silica gel column chromatography eluting with hexane:ethyl acetate=5:1 (v/v) to give 1.56 g (yield: 78%) of a colorless powder (7a).

mp: 146°–147° C.

Anal. Calcd for C$_{28}$H$_{46}$O$_3$: C, 78.09; H, 10.77

Found C, 78.27; H, 10.77

IR (KBr) cm$^{-1}$: 3459, 2952, 1467

$^1$H-NMR (CDCl$_3$) δ (ppm):

0.73 (3H, s), 0.82 (3H, s), 0.89 (6H, d, J=6 Hz), 1.67 (3H, s), 1.90 (1H, t, J=6 Hz), 2.30 (1H, t, J=10 Hz), 3.59 (1H, dd, J=10 and 5 Hz), 3.93 (4H, s), 5.52 (1H, t, J=6 Hz)

FABMS (+KI) m/z: 469 (MK$^+$)

(6) Syntheses of Compound (8a) and Compound (9a)

1.2 g of Compound (7a) was dissolved in 30 ml of methylene chloride under a nitrogen atmosphere, and then 15 mg of vanadyl acetylacetonate was added thereto, followed by stirring at room temperature for 10 minutes. After ice-cooling the solution, 1.7 ml of tert-butyl hydroperoxide (3.3N, methylene chloride solution) was added dropwise thereto, and the mixture was warmed to room temperature and stirred for 2 hours. The reaction solution was diluted with diethyl ether, passed through a short column with Florisil and concentrated. The resulting crude product was subjected to silica gel flash column chromatography eluting with hexane:ethyl acetate=3:1 (v/v), thereby 54 mg (yield: 4%) of a colorless powder (9a) was obtained from earlier eluting fractions, and 860 mg (yield: 68%) of a colorless powder (8a) was obtained from later eluting fractions.

Compound (8a)

mp: 130°–132° C.

Anal. Calcd for C$_{28}$H$_{46}$O$_4$: C, 75.29; H, 10.38

Found: C, 75.25; H, 10.50

IR (KBr) cm$^{-1}$: 3455, 3338, 2937, 1105, 1073 1021

$^1$H-NMR (CDCl$_3$) δ (ppm):

0.70 (3H, s), 0.79 (3H, s), 0.94 (3H, d, J=7 Hz), 0.97 (3H, d, J=7 Hz), 1.27 (3H, s), 3.23 (1H, dd, J=11 and 5 Hz), 3.34 (1H, t, J=7 Hz), 3.92 (4H, s)

FABMS m/z: 447 (MH$^+$)

Compound (9a)

mp: 105°–108° C.

Anal. Calcd for C$_{28}$H$_{46}$O$_4$: C, 75.29; H, 10.38

Found: C, 75.48; H, 10.48

IR (KBr) cm$^{-1}$: 3468, 2948, 2872, 1469, 1073

$^1$H-NMR (CDCl$_3$) δ (ppm):

0.82 (3H, s), 0.84 (3H, s), 0.94 (3H, d, J=5 Hz), 0.97 (3H, d, J=5 Hz), 1.27 (3H, s), 2.76 (1H, t, J=6 Hz), 3.17 (1H, dd, J=10 and 4 Hz), 3.92 (4H, s), 4.42 (1H, s)

FABMS (+KI) m/z: 485 (MK$^+$)

(7) Synthesis of Compound (10a)

100 mg of Compound (8a) was dissolved in 2 ml of toluene, and then 60 mg of aluminum tert-butoxide was added thereto, followed by heating under reflux for 2 hours. After dilution of the reaction solution with diethyl ether, 300 μl of a saturated aqueous magnesium sulfate solution was added thereto, and the mixture was vigorously stirred at room temperature. To the mixture was added an excess amount of anhydrous magnesium sulfate, followed by stirring for 10 minutes. After filtration and concentration, the resulting product was purified by silica gel column chromatography eluting with hexane:ethyl acetate=5:1 (v/v) to give 59 mg (yield: 59%) of a colorless powder (10a).

mp: 222°–223° C.

Anal. Calcd for $C_{28}H_{46}O_4$: C, 75.29; H, 10.38

Found: C, 75.50; H, 10.52

IR (KBr) $cm^{-1}$: 3310, 2950, 2868, 1358

$^1$H-NMR (CDCl$_3$) δ (ppm):

0.73 (3H, s), 0.82 (3H, s), 0.91 (3H, d, J=5 Hz), 0.92 (3H, d, J=5 Hz), 3.47 (1H, dd, J=10 and 4 Hz), 3.94 (4H, s), 4.25 (1H, t, J=7 Hz), 4.93 (1H, s), 5.09 (1H, s)

FABMS (+KI) m/z: 485 (MK$^+$)

(8) Synthesis of Compound (11a)

0.28 g of Compound (10a) was dissolved in 6.9 ml of methylene chloride, the solution was cooled on an ice water bath, and 0.065 g of sodium bicarbonate and 0.188 g of m-chloroperbenzoic acid were added thereto. The mixture was stirred for 4 hours and further stirred at room temperature for 6 hours. To the reaction solution was added an aqueous sodium thiosulfate solution, and the mixture was extracted with ethyl acetate. The extract was successively washed with a saturated aqueous sodium bicarbonate solution and a saturated aqueous sodium chloride solution and dried over anhydrous magnesium sulfate. After evaporation of the solvent, the resulting crude product was subjected to silica gel column chromatography eluting with hexane:ethyl acetate=3:2 (v/v) to give fractions of Compound (11a). After evaporation of the solvent, recrystallization from ethyl acetate—hexane gave 0.17 g (yield: 58%) of colorless fine needles (11a).

mp: 174°–176° C.

Anal. Calcd for $C_{28}H_{46}O_5$: C, 72.69; H, 10.02

Found: C, 72.83; H, 10.12

IR (KBr) $cm^{-1}$: 3368, 2948, 2870, 1096

$^1$H-NMR (CDCl$_3$) δ (ppm):

0.68 (3H, s), 0.80 (3H, s), 0.91 (3H, d, J=6 Hz), 0.94 (3H, d, J=6 Hz), 2.14 (1H, t, J=8 Hz), 2.88 (1H, d, J=4 Hz), 3.06 (1H, d, J=4 Hz), 3.36 (1H, dd, J=10 and 5 Hz), 3.44 (1H, dd, J=10 and 4 Hz), 3.93 (4H, s), 4.14 (1H, br s)

LSIMS (+KI) m/z: 501 (MK$^+$)

(9) Synthesis of Compound (12a)

0.23 g of Compound (11a) was dissolved in 10 ml of 80% (w/w) aqueous acetic acid solution, followed by stirring at room temperature for an hour. The reaction solution, after addition of water, was extracted with ethyl acetate, successively washed with a saturated aqueous sodium bicarbonate solution and a saturated aqueous sodium chloride solution and dried over anhydrous magnesium sulfate. After evaporation of the solvent, the resulting crude product was purified by silica gel column chromatography eluting with hexane:ethyl acetate=1:1 (v/v) to give 0.13 g (yield: 63%) of a colorless powder (12a).

mp: 188°–190° C.

Anal. Calcd for $C_{26}H_{42}O_4$: C, 74.60; H, 10.11

Found: C, 74.73; H, 10.26

IR (KBr) $cm^{-1}$: 3426, 2943, 2869, 1708, 1030

$^1$H-NMR (CDCl$_3$) δ (ppm):

0.72 (3H, s), 0.90 (3H, d, J=6 Hz), 0.95 (3H, d, J=6 Hz), 1.00 (3H, s), 2.89 (1H, d, J=4 Hz), 3.07 (1H, d, J=4 Hz), 3.39 (1H, dd, J=10 and 4 Hz), 3.45 (1H, dd, J=10 and 4 Hz), 4.21 (1H, br s)

LSIMS (+KI) m/z: 457 (MK$^+$)

An alternative synthesis method of Compound (10a) is described as follows:

(10) Synthesis of Compound (13a)

3.51 g of Compound (8a) was dissolved in 40 ml of pyridine, and then 3.7 ml of acetic anhydride and 0.48 g of 4-dimethylaminopyridine were added thereto, followed by stirring at room temperature for 3 hours. The reaction solution, after addition of ethyl acetate, was successively washed with dil. hydrochloric acid, a saturated aqueous sodium bicarbonate solution and a saturated aqueous sodium chloride solution and dried over anhydrous magnesium sulfate. After evaporation of the solvent, the resulting crude product was purified by silica gel column chromatography eluting with hexane:ethyl acetate=5:1 (v/v) to give 3.61 g (yield: 94%) of a colorless powder (13a).

mp: 169°–171° C.

Anal. Calcd for $C_{30}H_{48}O_5$: C, 73.73; H, 9.90

Found: C, 73.83; H, 9.96

IR (KBr) $cm^{-1}$: 2957, 2930, 1731, 1245

$^1$H-NMR (DMSO-d$_6$) δ (ppm):

0.75 (3H, s), 0.79 (3H, s), 0.90 (6H, d, J=6 Hz), 1.15 (3H, s), 2.00 (3H, s), 2.44 (1H, dd, J=9 and 3 Hz), 3.82 (4H, s), 4.53 (1H, dd, J=11 and 5 Hz)

LSIMS m/z: 489 (MH$^+$)

(11) Syntheses of Compound (14a) and Compound (15a)

To 0.41 g of Compound (13a) was added 16 ml of 0.01N hydrogen chloride solution in ethyl acetate, followed by stirring at room temperature for an hour. The reaction solution, after addition of a saturated aqueous sodium bicarbonate solution, was extracted with ethyl acetate, washed with a saturated aqueous sodium chloride solution and dried over anhydrous magnesium sulfate. After evaporation of the solvent, the resulting crude product was purified by silica gel column chromatography eluting with hexane:ethyl acetate= 4:1 (v/v) to give 0.40 g (yield: 97%) of a mixture of Compound (14a) and Compound (15a), a part of which was then separated by silica gel column chromatography eluting with hexane:ethyl acetate=5:1 (v/v), thereby a colorless powder (15a) was obtained from earlier eluting fractions, and a colorless powder (14a) was obtained from later eluting fractions.

Compound (14a)

mp: 68°–70° C.

IR (KBr) $cm^{-1}$: 3502, 1714, 1371, 1268

$^1$H-NMR (CDCl$_3$) δ (ppm):

0.82 (3H, s), 0.89 (3H, d, J=6 Hz), 0.91 (3H, d, J=6 Hz), 0.93 (3H, s), 1.92 (3H, s), 2.33 (1H, dd, J=10 and 8 Hz), 3.92 (4H, s), 3.98–4.08 (1H, m), 4.67 (1H, dd, J=10 and 5 Hz), 4.97 (1H, s), 5.02 (1H, s)

LSIMS (+KI) m/z: 527 (MK$^+$)

Compound (15a)

mp: 143°–149° C.

IR (KBr) $cm^{-1}$: 3508, 1737, 1368, 1240

$^1$H-NMR (CDCl$_3$) δ (ppm):

0.78 (3H, s), 0.83 (3H, s), 0.91 (3H, d, J=6 Hz), 0.93 (3H, d, J=6 Hz), 2.06 (3H, s), 2.22 (1H, t, J=10 Hz), 3.47 (1H, dd, J=10 and 5 Hz), 3.93 (4H, s), 5.17 (1H, s), 5.27 (1H, s), 5.40 (1H, t, J=6 Hz)

LSIMS (+KI) m/z: 527 (MK$^+$)

(12) Synthesis of Compound (10a)

3.08 g of the mixture of Compound (14a) and Compound (15a) was dissolved in 90 ml of methanol, and 1.75 g of anhydrous potassium carbonate was added thereto, followed by stirring at room temperature for 10 hours. After evaporation of the reaction solution, water was added to the resulting residue, and the mixture was extracted with methylene chloride, washed with a saturated aqueous sodium chloride solution and dried over anhydrous magnesium sulfate. After evaporation of the solvent, the resulting crude product was purified by silica gel column chromatography eluting with methylene chloride:ethyl acetate=4:1 (v/v) to give 2.72 g (97%) of Compound (10a).

EXAMPLE 2

(cases of the compounds wherein R is an isopentyl group, X and Y are connected together to form an ethylenedioxy group in Schemes 1 and 2)

(1) Syntheses of Compound (3b) and Compound (4b)

A colorless oil (3b) and a colorless oil (4b) were obtained from Compound (2) according to the preparation method described in Example 1 (2).

Compound (3b)

IR (neat) $cm^{-1}$: 3429, 2948, 1152, 1101, 1050, 1024, 756

$^1$H-NMR (CDCl$_3$) δ (ppm):

0.83 (3H, s), 0.85 (3H, s), 0.87 (6H, d, J=7 Hz), 1.19 (3H, s), 3.36 (3H, s), 3.42 (3H, s), 4.68 (2H, s), 4.71 (1H, d, J=7 Hz), 4.84 (1H, d, J=7 Hz), 5.19 (1H, br s)

FABMS (+KI) m/z: 547 (MK$^+$)

Compound (4b)

IR (neat) $cm^{-1}$: 3430, 2932, 1151, 1102, 1049, 1025, 756

$^1$H-NMR (CDCl$_3$) δ (ppm):

0.82 (3H, s), 0.83 (3H, s), 0.87 (6H, d, J=7 Hz), 1.05 (3H, s), 3.36 (3H, s), 3.42 (3H, s), 4.68 (2H, s), 4.71 (1H, d, J=7 Hz), 4.78 (1H, br s), 4.84 (1H, d, J=7 Hz)

FABMS (+KI) m/z: 547 (MK$^+$)

(2) Synthesis of Compound (5b)

A colorless powder (5b) was obtained from a mixture of Compound (3b) and Compound (4b) according to the preparation method described in Example 1 (3).

mp: 162°–164° C.

Anal. Calcd for $C_{27}H_{46}O_2$: C, 80.54; H, 11.52

Found: C, 80.51; H, 11.44

IR (KBr) $cm^{-1}$: 3469, 2950, 2926, 2868, 1470

$^1$H-NMR (CDCl$_3$) δ (ppm):

0.74 (3H, s), 0.82 (3H, s), 0.88 (6H, d, J=6 Hz), 1.68 (3H, s), 2.01 (1H, dt, J=7 Hz), 2.28 (1H, t, J=9 Hz), 3.48–3.68 (2H, m), 5.48 (1H, t, J=7 Hz)

LSIMS (+KI) m/z: 441 (MK$^+$)

(3) Synthesis of Compound (6b)

A colorless powder (6b) was obtained from Compound (5b) according to the preparation method described in Example 1 (4).

IR (KBr) $cm^{-1}$: 3554, 3436, 2950, 1720, 1384, 1020

$^1$H-NMR (CDCl$_3$) δ (ppm):

0.77 (3H, s), 0.87 (6H, d, J=7 Hz), 1.02 (3H, s), 1.69 (3H, br s), 3.61 (1H, dd, J=11 and 4 Hz), 5.49 (1H, br d, J=6 Hz)

LSIMS (+KI) m/z: 439 (MK$^+$)

(4) Synthesis of Compound (7b)

A colorless powder (7b) was obtained from Compound (6b) according to the preparation method described in Example 1 (5).

mp: 116°–118° C.

IR (KBr) $cm^{-1}$: 3459, 2952, 2934, 1383, 1099, 1071, 1014

$^1$H-NMR (CDCl$_3$) δ (ppm):

0.72 (3H, s), 0.83 (6H, d, J=7 Hz), 0.88 (3H, s), 1.68 (3H, br s), 2.27 (1H, br t, J=9 Hz), 3.58 (1H, dd, J=11 and 5 Hz), 3.92 (4H, s), 5.49 (1H, br d, J=6 Hz)

LSIMS (+KI) m/z: 445 (MH$^+$)

(5) Syntheses of Compound (8b) and Compound (9b)

A colorless powder (8b) and a colorless powder (9b) were obtained at the yield ratio of about 5:1 from Compound (7b) according to the preparation method described in Example 1 (6).

Compound (8b)

mp: 115°–118° C.

IR (KBr) $cm^{-1}$: 3436, 2947, 2871, 1385, 1137, 1098, 1072, 1022

$^1$H-NMR (CDCl$_3$) δ (ppm):

0.69 (3H, s), 0.80 (3H, s), 0.89 (6H, d, J=7 Hz), 1.29 (3H, s), 3.19–3.32 (2H, m), 3.92 (4H, s)

LSIMS m/z: 461 (MH$^+$)

Compound (9b)

mp: 79°–82° C.

IR (KBr) $cm^{-1}$: 3436, 2952, 2872, 1386, 1136, 1102, 1072, 1026

$^1$H-NMR (CDCl$_3$) δ (ppm):

0.82 (3H, s), 0.85 (3H, s), 0.91 (6H, d, J=7 Hz), 1.30 (3H, s), 2.71 (1H, t, J=6 Hz), 3.18 (1H, dd, J=11 and 4 Hz), 3.92 (4H, s)

LSIMS (+KI) m/z: 461 (MH$^+$)

(6) Synthesis of Compound (10b)

A colorless powder (10b) was obtained from Compound (8b) according to the preparation method described in Example 1 (7).

mp: 144°–145° C.

IR (KBr) $cm^{-1}$: 3269, 2945, 2870, 1359, 1112, 1096, 1073, 1024, 901

$^1$H-NMR (CDCl$_3$) δ (ppm):

0.74 (3H, s), 0.81 (3H, s), 0.87 (6H, d, J=7 Hz), 2.34 (1H, br t, J=10 Hz), 3.42–3.54 (1H, m), 3.92 (4H, s), 4.10 (1H, t, J=6 Hz), 4.93 (1H, s), 5.07 (1H, s)

LSIMS (+KI) m/z: 499 (MK$^+$)

(7) Synthesis of Compound (11b)

Colorless needles (11b) were obtained from Compound (10b) according to the preparation method described in Example 1 (8).

mp: 148°–150° C.

Anal. Calcd for $C_{29}H_{48}O_5$: C, 73.08; H, 10.14

Found: C, 72.85; H, 10.28

IR (KBr) $cm^{-1}$: 3392, 2946, 2869, 1096, 1073 1030

$^1$H-NMR (CDCl$_3$) δ (ppm):

0.69 (3H, s), 0.80 (3H, s), 0.88 (3H, d, J=6 Hz), 0.89 (3H, d, J=6 Hz), 2.15 (1H, br t, J=8 Hz), 2.85 (1H, d, J=4 Hz), 3.06 (1H, d, J=4 Hz), 3.27–3.35 (1H, m), 3.37 (1H, dd, J=11 and 4 Hz), 3.92 (4H, s)

LSIMS m/z: 477 (MH$^+$)

(8) Synthesis of Compound (12b)

A colorless powder (12b) was obtained from Compound (11b) according to the preparation method described in Example 1 (9).

IR (KBr) $cm^{-1}$: 3401, 2951, 2869, 1703, 1028

$^1$H-NMR (CDCl$_3$) δ (ppm):

0.71 (3H, s), 0.88 (3H, d, J=7 Hz), 0.90 (3H, d, J=7 Hz), 1.00 (3H, s), 2.86 (1H, d, J=4 Hz), 3.07 (1H, d, J=4 Hz), 3.30 (1H, dd, J=10 and 4 Hz), 3.41 (1H, dd, J=10 and 4 Hz)

EIMS m/z: 432 (M$^+$, 0.89%), 272 (base)

High resolution EIMS m/z:

Calcd for $C_{27}H_{44}O_4$: 432.3240

Found: 432.3235

(9) Alternative synthesis of Compound(10b)

Compound (10b) was obtained from Compound (8b) according to the preparation methods described in Example 1 (10), (11) and (12).

EXAMPLE 3

(cases where R is a methyl group, and X is an ethylenedioxy group in Schemes 1 and 2)

(1) Syntheses of Compound (3c) and Compound (4c)

A colorless oil (3c) and a colorless oil (4c) were obtained from Compound (2) according to the preparation method described in Example 1 (2).

Compound (3c)

IR (neat) cm$^{-1}$: 3429, 2932, 1447, 1383, 1214, 1152

$^1$H-NMR (CDCl$_3$) δ (ppm):

0.82 (3H, s), 0.87 (3H, s), 0.89 (3H, t, J=6 Hz), 1.19 (3H, s), 3.37 (3H, s), 3.41 (3H, s), 3.30–3.60 (2H, m), 4.68 (2H, s), 4.70 (1H, d, J=6 Hz), 4.85 (1H, d, J=6 Hz), 5.19 (1H, br s)

LSIMS (+KI) m/z: 491 (MK$^+$)

Compound (4c)

IR (neat) cm$^{-1}$: 3435, 2930, 1465, 1447, 1384, 1152

$^1$H-NMR (CDCl$_3$) δ (ppm):

0.87 (3H, s), 0.88 (3H, s), 0.89 (3H, t, J=6 Hz), 1.02 (3H, s), 3.36 (3H, s), 3.41 (3H, s), 3.30–3.60 (2H, m), 4.68 (2H, s), 4.70 (1H, d, J=6 Hz), 4.83 (1H, d, J=6 Hz)

LSIMS (+KI) m/z: 491 (MK$^+$)

(2) Synthesis of Compound (5c)

A colorless powder (5c) was obtained from a mixture of Compound (3c) and Compound (4c) according to the preparation method described in Example 1 (3).

mp: 150°–151° C.

IR (KBr) cm$^{-1}$: 3306, 2927, 2856, 1449, 1382, 1043

$^1$H-NMR (CDCl$_3$) δ (ppm):

0.73 (3H, s), 0.82 (3H, s), 1.57 (3H, s), 2.20–2.40 (1H, m), 3.48–3.70 (2H, m), 5.57 (1H, q, J=6 Hz)

EIMS m/z: 346 (M$^+$, 18.0%), 328 (base)

(3) Synthesis of Compound (6c)

A colorless powder (6c) was obtained from Compound (5c) according to the preparation method described in Example 1 (4).

mp: 155°–161° C.

IR (KBr) cm$^{-1}$: 3540, 3436, 2941, 2916, 2860, 1716

$^1$H-NMR (CDCl$_3$) δ (ppm):

0.75 (3H, s), 1.01 (3H, s), 1.59 (3H, s), 1.60 (3H, d, J=6 Hz), 3.60 (1H, dd, J=12 and 5 Hz), 5.57 (1H, q, J=6 Hz)

LSIMS m/z: 345 (MH$^+$)

(4) Synthesis of Compound (7c)

A colorless powder (7c) was obtained from Compound (6c) according to the preparation method described in Example 1 (5).

mp: 173°–177° C.

IR (KBr) cm$^{-1}$: 3477, 2946, 1383, 1096, 1072

$^1$H-NMR (CDCl$_3$) δ (ppm):

0.73 (3H, s), 0.82 (3H, s), 1.60 (3H, t, J=6 Hz), 1.64 (3H, s), 2.20–2.40 (1H, m), 3.57 (1H, dd, J=8 and 3 Hz), 3.93 (4H, s), 5.58 (1H, q, J=5 Hz)

LSIMS m/z: 381 (MH$^+$)

(5) Syntheses of Compound (8c) and Compound (9c)

A colorless powder (8c) and a colorless powder (9c) were obtained at the yield ratio of about 5:1 from Compound (7c) according to the preparation method described in Example 1 (6).

Compound (8c)

mp: 152°–157° C.

IR (KBr) cm$^{-1}$: 3468, 2941, 1455, 1386, 1103, 1069

LSIMS m/z: 405 (MH$^+$)

Compound (9c)

mp: 154°–156° C.

IR (KBr) cm$^{-1}$: 3468, 2944, 1445, 1072

$^1$H-NMR (CDCl$_3$) δ (ppm):

0.81 (3H, s), 0.84 (3H, s), 1.28 (3H, d, J=5 Hz), 1.30 (3H, s), 2.88 (1H, q, J=5 Hz), 3.17 (1H, dd, J=8 and 5 Hz), 3.92 (4H, s)

LSIMS m/z: 405 (MH$^+$)

(6) Synthesis of Compound (10c)

A colorless powder (10c) was obtained from Compound (8c) according to the preparation method described in Example 1 (7).

mp: 208°–211° C.

IR (KBr) cm$^{-1}$: 3272, 2927, 1359, 1097, 1071

$^1$H-NMR (CDCl$_3$) δ (ppm):

0.75 (3H, s), 0.84 (3H, s), 1.28 (3H, d, J=5 Hz), 2.42 (1H, t, J=8 Hz), 3.54 (1H, dd, J=8 and 4 Hz), 3.95 (4H, s), 4.47 (1H, q, J=5 Hz), 4.90 (1H, s), 5.14 (1H, s)

FABMS m/z: 405 (MH$^+$)

(7) Synthesis of Compound (11c)

A colorless powder (11c) was obtained from Compound (10c) according to the preparation method described in Example 1 (8).

mp: 188°–196° C.

IR (KBr) cm$^{-1}$: 3436, 2942, 1374, 1103, 1071, 1028

$^1$H-NMR (CDCl$_3$) δ (ppm):

0.70 (3H, s), 0.81 (3H, s), 1.28 (3H, d, J=5 Hz), 2.10 (1H, t, J=8 Hz), 2.95 (1H, d, J=3 Hz), 3.08 (1H, d, J=3 Hz), 3.35 (1H, dd, J=8 and 4 Hz), 3.64 (1H, q, J=5 Hz), 3.94 (4H, s)

FABMS m/z: 421 (MH$^+$)

(8) Synthesis of Compound (12c)

A colorless powder (12c) was obtained from Compound (11c) according to the preparation method described in Example 1 (9).

mp: 155°–160° C.

IR (KBr) cm$^{-1}$: 2949, 1698, 1076, 1028

$^1$H-NMR (CDCl$_3$) δ (ppm):

0.73 (3H, s), 1.00 (3H, s), 1.26 (3H, d, J=5 Hz), 2.96 (1H, d, J=3 Hz), 3.09 (1H, d, J=3 Hz), 3.38 (1H, dd, J=8 and 4 Hz), 3.64 (1H, q, J=5 Hz)

LSIMS m/z: 377 (MH$^+$)

An alternative method for preparing Compound (10c) is described as follows:

(9) Synthesis of Compound (13c)

A colorless powder (13c) was obtained from Compound (8c) according to the preparation method described in Example 1 (10).

mp: 177°–182° C.

IR (KBr) cm$^{-1}$: 2952, 1730, 1376, 1249, 1094, 1021

$^1$H-NMR (acetone-d$_6$) δ (ppm):

0.84 (3H, s), 0.90 (3H, s), 1.18 (3H, d, J=4 Hz), 1.21 (3H, s), 2.04 (3H, s), 2.59 (1H, q, J=4 Hz), 3.88 (4H, s), 4.57 (1H, dd, J=8 and 4 Hz)

LSIMS m/z: 447 (MH$^+$)

(10) Syntheses of Compound (14c) and Compound (15c)

A colorless powder (14c) and a colorless powder (15c) were obtained from Compound (13c) according to the preparation method described in Example 1 (11).

Compound (14c)

mp: 163°–167° C.

IR (KBr) cm$^{-1}$: 1717, 1373, 1260, 1101

$^1$H-NMR (acetone-d$_6$) δ (ppm):

0.86 (3H, s), 1.22 (3H, d, J=4 Hz), 1.86 (3H, s), 2.46 (1H, t, J=8 Hz), 3.87 (4H, s), 3.98 (1H, q, J=4 Hz), 4.55 (1H, dd, J=8 and 4 Hz), 4.90 (1H, s), 5.11 (1H, s)

FABMS m/z: 447 (MH$^+$)

Compound (15c)

mp: 116°–118° C.

IR (KBr) cm$^{-1}$: 3460, 2933, 1730, 1372, 1243, 1073

$^1$H-NMR (acetone-d$_6$) δ (ppm):

0.68 (3H, s), 0.84 (3H, s), 1.28 (3H, d, J=5 Hz), 1.96 (3H, s), 2.25 (1H, t, J=8 Hz), 3.35–3.48 (1H, m), 3.88 (4H, s), 5.08 (1H, s), 5.25 (1H, s), 5.60 (1H, q, J=5 Hz)

FABMS m/z: 447 (MH$^+$)

(11) Synthesis of Compound (10c)

A colorless powder (10c) was obtained from a mixture of Compound (14c) and Compound (15c) according to the preparation method described in Example 1 (12).

EXAMPLE 4

(cases where R is a tridecyl group and X and Y are connected together to form an ethylenedioxy group in Schemes 1 and 2)

(1) Syntheses of Compound (3d) and Compound (4d)

A colorless oil (3d) and a colorless oil (4d) were obtained from Compound (2) according to the preparation method described in Example 1 (2).

Compound (3d)

IR (neat) cm$^{-1}$: 3430, 2921, 2851, 1464, 1152, 1050

$^1$H-NMR (CDCl$_3$) δ (ppm):

0.81 (3H, s), 0.85 (3H, s), 0.88 (3H, t, J=5 Hz), 1.20 (3H, s), 3.30–3.60 (2H, m), 3.37 (3H, s), 3.40 (3H, s), 4.67 (2H, s), 4.71 (1H, d, J=5 Hz), 4.85 (1H, d, J=5 Hz)

FABMS (+KI) m/z: 659 (MK$^+$)

Compound (4d)

IR (neat) cm$^{-1}$: 2926, 1151, 1102, 1050, 1025

$^1$H-NMR (CDCl$_3$) δ (ppm):

0.83 (3H, s), 0.84 (3H, s), 0.88 (3H, t, J=5 Hz), 1.04 (3H, s), 3.30–3.60 (2H, m), 3.37 (2H, s), 3.42 (2H, s), 4.68 (2H, s), 4.71 (1H, d, J=5 Hz), 4.84 (1H, d, J=5 Hz)

LSIMS (+KI) m/z: 659 (MK$^+$)

(2) Synthesis of Compound (5d)

A colorless powder (5d) was obtained from a mixture of Compound (3d) and Compound (4d) according to the preparation method described in Example 1 (3).

mp: 82°–84° C.

IR (KBr) cm$^{-1}$: 3441, 2917, 2850, 1469

$^1$H-NMR (CDCl$_3$) δ (ppm):

0.74 (3H, s), 0.82 (3H, s), 0.87 (3H, t, J=5 Hz), 1.68 (3H, s), 2.28 (1H, t, J=8 Hz), 3.50–3.70 (2H, m), 5.50 (1H, t, J=5 Hz)

LSIMS (+KI) m/z: 553 (MK$^+$)

(3) Synthesis of Compound (6d)

A colorless powder (6d) was obtained from Compound (5d) according to the preparation method described in Example 1 (4).

mp: 88°–91° C.

IR (KBr) cm$^{-1}$: 2922, 1720, 1469

$^1$H-NMR (CDCl$_3$) δ (ppm):

0.76 (3H, s), 0.88 (3H, t, J=5 Hz), 1.02 (3H, s), 1.68 (3H, s), 3.61 (1H, dd, J=8 and 4 Hz), 5.50 (1H, t, J=5 Hz)

LSIMS m/z: 513 (MH$^+$)

(4) Synthesis of Compound (7d)

A colorless powder (7d) was obtained from Compound (6d) according to the preparation method described in Example 1 (5).

mp: 89°–91° C.

IR (KBr) cm$^{-1}$: 3459, 2918, 1472

$^1$H-NMR (CDCl$_3$) δ (ppm):

0.74 (3H, s), 0.82 (3H, s), 0.88 (3H, t, J=5 Hz), 1.67 (3H, s), 2.28 (1H, t, J=8 Hz), 3.58 (1H, dd, J=8 and 4 Hz), 3.93 (4H, s), 5.50 (1H, t, J=5 Hz)

LSIMS m/z: 557 (MH$^+$)

(5) Syntheses of Compound (8d) and Compound (9d)

A colorless powder (8d) and a colorless powder (9d) were obtained at a ratio of about 8:1 from Compound (7d) according to the preparation method described in Example 1 (6).

Compound (8d)

IR (KBr) cm$^{-1}$: 3435, 2922, 2852, 1469, 1072

$^1$H-NMR (CDCl$_3$) δ (ppm):

0.70 (3H, s), 0.80 (3H, s), 0.88 (3H, t, J=5 Hz), 3.18–3.34 (2H, m), 3.93 (4H, s), 4.42 (1H, s)

FABMS m/z: 573 (MH$^+$)

Compound (9d)

mp: 88°–91° C.

IR (KBr) cm$^{-1}$: 3486, 2921, 1471

$^1$H-NMR (CDCl$_3$) δ (ppm):

0.82 (3H, s), 0.84 (3H, s), 0.89 (3H, t, J=5 Hz), 2.71 (1H, t, J=6 Hz), 3.18 (1H, dd, J=8 and 4 Hz), 3.92 (4H, s)

FABMS m/z: 573 (MH$^+$)

(6) Synthesis of Compound (10d)

A colorless powder (10d) was obtained from Compound (8d) according to the preparation method described in Example 1 (7).

mp: 130°–131° C.

IR (KBr) cm$^{-1}$: 3294, 2926, 1358, 1073

$^1$H-NMR (CDCl$_3$) δ (ppm):

0.74 (3H, s), 0.83 (3H, s), 0.88 (3H, t, J=5 Hz), 2.32 (1H, t, J=8 Hz), 3.48 (1H, dd, J=8 and 4 Hz), 3.93 (4H, s), 4.13 (1H, t, J=5 Hz), 4.93 (1H, s), 5.08 (1H, s)

LSIMS m/z: 573 (MH$^+$)

(7) Synthesis of Compound (11d)

A colorless powder (11d) was obtained from Compound (10d) according to the preparation method described in Example 1 (8).

mp: 80°–82° C.

IR (KBr) cm$^{-1}$: 3401, 2922, 1471, 1072

$^1$H-NMR (CDCl$_3$) δ (ppm):

0.70 (3H, s), 0.81 (3H, s), 0.88 (3H, t, J=5 Hz), 2.87 (1H, d, J=3 Hz), 3.06 (1H, d, J=3 Hz), 3.30–3.42 (2H, m), 3.93 (4H, s)

FABMS m/z: 589 (MH$^+$)

(8) Synthesis of Compound (12d)

A colorless powder (12d) was obtained from Compound (11d) according to the preparation method described in Example 1 (9).

mp: 125°–129° C.

IR (KBr) cm$^{-1}$: 3411, 2924, 1709, 1262, 1029

$^1$H-NMR (CDCl$_3$) δ (ppm):

0.82 (3H, s), 0.88 (3H, t, J=5 Hz), 1.00 (3H, s), 2.89 (1H, d, J=3 Hz), 3.07 (1H, d, J=3 Hz), 3.31–3.45 (2H, m)

LSIMS (+KI) m/z: 583 (MK$^+$)

An alternative synthesis of Compound (10d) is described as follows:

(9) Synthesis of Compound (13d)

A colorless powder (13d) was obtained from Compound (8d) according to the preparation method described in Example 1 (10).

mp: 104°–107° C.

IR (KBr) cm$^{-1}$: 2922, 1728, 1255

$^1$H-NMR (acetone-d$_6$) δ (ppm):

0.83 (3H, s), 0.88 (3H, t, J=5 Hz), 0.89 (3H, s), 1.21 (3H, s), 2.03 (3H, s), 3.85 (4H, s), 4.60 (1H, dd, J=8 and 4 Hz)

FABMS m/z: 615 (MH$^+$)

(10) Syntheses of Compound (14d) and Compound (15d)

A mixture of a colorless powdery Compound (14d) and a colorless powdery Compound (15d) was obtained from Compound (13d) according to the preparation method described in Example 1 (11).

Compound (14d)

$^1$H-NMR (CDCl$_3$) δ (ppm):

0.78 (3H, s), 0.81 (3H, s), 0.88 (3H, t, J=5 Hz), 1.91 (3H, s), 3.82–3.95 (1H, m), 3.95 (4H, s), 4.68 (1H, dd, J=8 and 4 Hz), 4.98 (1H, s), 5.02 (1H, s)

Compound (15d)

$^1$H-NMR (CDCl$_3$) δ (ppm):

0.82 (3H, s), 0.88 (3H, t, J=5 Hz), 0.91 (3H, s), 2.06 (3H, s), 3.48 (1H, dd, J=8 and 4 Hz), 3.94 (4H, s), 5.19 (1H, s), 5.24 (1H, s), 5.27 (1H, t, J=6 Hz)

(11) Synthesis of Compound (10d)

A colorless powder (10d) was obtained from a mixture of Compound (14d) and Compound (15d) according to the preparation method described in Example 1 (12).

EXAMPLE 5

(cases of the compounds wherein R is an isobutyl group in Scheme 3)

(1) Syntheses of Compound (16a) and Compound (17a)

0.2 g of Compound (5a) was dissolved in 6.5 ml of methylene chloride under a nitrogen atmosphere, 0.001 g of vanadyl acetylacetonate was added thereto, and the mixture was cooled on an ice water bath. To the solution was added 0.25 ml of tert-butyl hydroperoxide (3.3N methylene chloride solution), and the mixture was stirred for an hour and then further stirred at room temperature for 5 hours. The reaction solution was diluted with methylene chloride, and then after addition of Florisil, the mixture was passed through a short column with silica gel eluting with ethyl acetate. The resulting crude product was purified by silica gel column chromatography eluting with chloroform:ethyl acetate=5:1 (v/v) to give a mixture of 0.19 g of a colorless powdery Compound (16a) and a colorless powdery Compound (17a) [Compound (17a) is contained as a by-product in an amount of about 10% as a result of analysis by $^1$H-NMR spectra as a by-product]. The mixture was recrystallized from ethyl acetate—hexane to give 0.15 g (yield of 72%) of Compound (16a).

Compound (16a)

mp: 204°–207° C.

Anal. Calcd for C$_{26}$H$_{44}$O$_3$: C, 77.18; H, 10.96

Found: C, 77.14; H, 11.11

IR (KBr) cm$^{-1}$: 3386, 3284, 2948, 2871, 1045

$^1$H-NMR (CDCl$_3$) δ (ppm):

0.70 (3H, s), 0.78 (3H, s), 0.95 (3H, d, J=4 Hz), 0.98 (3H, d, J=4 Hz), 1.27 (3H, s), 3.23 (1H, dd, J=12 and 5 Hz), 3.35 (1H, t, J=6 Hz), 3.48–3.67 (1H, m), 4.50 (1H, s)

LSIMS (+KI) m/z: 443 (MK$^+$)

Compound (17a)

$^1$H-NMR (CDCl$_3$) δ (ppm):

0.82 (3H, s), 0.84 (3H, s), 0.93 (3H, d, J=5 Hz), 0.97 (3H, d, J=5 Hz), 2.75 (1H, t, J=6 Hz), 3.17 (1H, dd, J=12 and 5 Hz), 3.49–3.67 (1H, m), 4.42 (1H, s)

(2) Synthesis of Compound (18a)

A colorless powder (18a) was obtained from Compound (16a) according to the preparation method described in Example 1 (7).

mp: 224°–226° C.

Anal. Calcd for C$_{26}$H$_{44}$O$_3$: C, 77.18; H, 10.96

Found: C, 77.28; H, 11.16

IR (KBr) cm$^{-1}$: 3368, 2953, 2931, 2868, 1468

$^1$H-NMR (CDCl$_3$) δ (ppm):

0.75 (3H, s), 0.84 (3H, s), 0.91 (3H, d, J=6 Hz), 0.93 (3H, d, J=6 Hz), 2.35 (1H, t, J=10 Hz), 3.07 (1H, br s), 3.48 (1H, dd, J=11 and 5 Hz), 3.50–3.70 (1H, m), 3.68 (1H, br s), 4.27 (1H, t, J=7 Hz), 4.95 (1H, s), 5.11 (1H, s)

FABMS (+KI) m/z: 443 (MK$^+$)

(3) Synthesis of Compound (19a)

A colorless powder (19a) was obtained from Compound (18a) according to the preparation method described in Example 1 (8).

mp: 169°–171° C.

Anal. Calcd for C$_{26}$H$_{44}$O$_4$: C, 74.24; H, 10.54

Found: C, 74.19; H, 10.76

IR (KBr) cm$^{-1}$: 3478, 3288, 2934, 2858, 1030

$^1$H-NMR (CDCl$_3$) δ (ppm):

0.67 (3H, s), 0.79 (3H, s), 0.92 (3H, d, J=6 Hz), 0.94 (3H, d, J=6 Hz), 2.13 (1H, t, J=8 Hz), 2.87 (1H, d, J=4 Hz), 3.06 (1H, d, J=4 Hz), 3.36 (1H, dd, J=12 and 5 Hz), 3.42 (1H, dd, J=10 and 4 Hz), 3.49–3.67 (1H, m)

FABMS (+KI) m/z: 459 (MK$^+$)

High resolution FABMS (+KI) m/z:

Calcd for C$_{26}$H$_{44}$O$_4$K: 459.2877 found: 459.2870

An alternative synthesis of Compound (18a) is described as follows:

(4) Synthesis of Compound (20a)

A colorless amorphous product (20a) was obtained from Compound (16a) according to the preparation method described in Example 1 (10).

Anal. Calcd for C$_{30}$H$_{48}$O$_5$: C, 73.73; H, 9.90

Found: C, 73.73; H, 9.98

IR (KBr) cm$^{-1}$: 2955, 1737, 1468, 1370, 1245, 1024

$^1$H-NMR (CDCl$_3$) δ (ppm):

0.83 (3H, s), 0.86 (3H, s), 0.95 (3H, d, J=7 Hz), 0.96 (3H, d, J=7 Hz), 1.24 (3H, s), 2.01 (3H, s), 2.04 (3H, s), 2.61 (1H, dd, J=9 and 2 Hz), 4.56–4.77 (2H, m)

LSIMS m/z: 489 (MH$^+$)

(5) Syntheses of Compound (21a) and Compound (22a)

A colorless amorphous product (21a) and a colorless powder (22a) were obtained from Compound (20a) according to the preparation method described in Example 1 (11).

Compound (21a)

Anal. Calcd for C$_{30}$H$_{48}$O$_5$: C, 73.73; H, 9.90

Found: C, 73.72; H, 10.06

IR (KBr) cm$^{-1}$: 3510, 2956, 1738, 1718, 1248, 1028

$^1$H-NMR (CDCl$_3$) δ (ppm):

0.83 (3H, s), 0.90 (3H, d, J=6 Hz), 0.92 (3H, d, J=6 Hz), 0.93 (3H, s), 1.93 (3H, s), 2.01 (3H, s), 2.32 (1H, t, J=10 Hz), 3.97–4.08 (1H, m), 4.58–4.76 (2H, m), 4.97 (1H, s), 5.03 (1H, s)

LSIMS (+KI) m/z: 527 (MK$^+$)

Compound (22a)

mp: 128°–130° C.

Anal. Calcd for C$_{30}$H$_{48}$O$_5$: C, 73.73; H, 9.90

Found: C, 73.86; H, 10.02

IR (KBr) cm$^{-1}$: 3470, 2954, 1734, 1714, 1264, 1024

$^1$H-NMR (CDCl$_3$) δ (ppm):

0.80 (3H, s), 0.85 (3H, s), 0.93 (3H, d, J=6 Hz), 0.95 (3H, d, J=6 Hz), 2.04 (3H, s), 2.08 (3H, s), 2.23 (1H, t, J=10 Hz), 3.50 (1H, dd, J=11 and 6 Hz), 4.57–4.78 (1H, m), 5.18 (1H, s), 5.28 (1H, s), 5.42 (1H, t, J=6 Hz)

LSIMS (+KI) m/z: 527 (MK$^+$)

(6) Synthesis of Compound (18a)

A colorless powder (18a) was obtained from a mixture of Compound (21a) and Compound (22a) according to the preparation method described in Example 1 (12).

EXAMPLE 6

(Syntheses of the compounds of Formula(I) of the present invention wherein the group easily hydrolyzable to a hydroxyl group is an N,N-dimethylglycyloxy group)

Syntheses of Compound (23a) (R is an isobutyl group, A is a hydroxyl group, X is an N,N-dimethylglycyloxy group and Y is a hydrogen atom), Compound (24a) (R is an isobutyl group, A is an N,N-dimethylglycyloxy group, X is a hydroxyl group and Y is a hydrogen atom) and Compound (25a) (R is an isobutyl group, A and X are each an N,N-dimethylglycyloxy group and Y is a hydrogen atom)

0.04 g of Compound (19a) was dissolved in 1.5 ml of methylene chloride, and then 0.012 g of N,N-dimethylglycine, 0.006 g of 4-dimethylaminopyridine and 0.027 g of 1-(3-dimethylaminopropyl)-3-ethylcarbodiimide hydrochloride were added thereto, followed by stirring at room temperature for 30 hours. The reaction solution, after addition of ethyl acetate, was successively washed with water and a saturated aqueous sodium chloride solution and dried over anhydrous magnesium sulfate. After evaporation of the solvent, the resulting residue was subjected to silica gel flash column chromatography eluting with ethyl acetate:methanol=30:1 (v/v), thereby 0.008 g (recovery: 20%) of a colorless powder (19a), 0.011 g (yield: 23%) of a colorless caramellike substance (23a), 0.006 g (yield: 13%) of a colorless caramellike substance (24a) and 0.016 g (yield: 29%) of a colorless caramellike substance (25a) were obtained in order of elution.

Compound (23a)

IR (KBr) cm$^{-1}$: 3396, 2952, 2870, 1744, 1468, 1204

$^1$H-NMR (CDCl$_3$) δ (ppm):

0.70 (3H, s), 0.83 (3H, s), 0.91 (3H, d, J=6 Hz), 0.96 (3H, d, J=6 Hz), 2.35 (6H, s), 2.96 (1H, d, J=5 Hz), 3.07 (1H, d, J=5 Hz), 3.13 (2H, s), 3.32–3.49 (2H, m), 4.19 (1H, br s), 4.69–4.88 (1H, m)

FABMS (+KI) m/z: 544 (MK$^+$)

Compound (24a)

IR (KBr) cm$^{-1}$: 3442, 2928, 2872, 1748, 1468, 1198, 1166, 1030

$^1$H-NMR (CDCl$_3$) δ (ppm):

0.67 (3H, s), 0.80 (3H, s), 0.91 (3H, d, J=5 Hz), 0.94 (3H, d, J=5 Hz), 2.36 (6H, s), 2.72 (1H, d, J=5 Hz), 3.08 (1H, d, J=5 Hz), 3.20 (2H, s), 3.33 (1H, dd, J=11 and 5 Hz), 3.50–3.68 (1H, m), 4.17 (1H, br s), 4.98 (1H, dd, J=10 and 4 Hz)

FABMS (+KI) m/z: 544 (MK$^+$)

Compound (25a)

IR (KBr) cm$^{-1}$: 3438, 2952, 2872, 1746, 1468, 1198, 1150

$^1$H-NMR (CDCl$_3$) δ (ppm):

0.67 (3H, s), 0.82 (3H, s), 0.91 (3H, d, J=5 Hz), 0.94 (3H, d, J=5 Hz), 2.34 (6H, s), 2.36 (6H, s), 2.72 (1H, d, J=4 Hz), 3.08 (1H, d, J=4 Hz), 3.14 (2H, s), 3.20 (2H, s), 3.33 (1H, dd, J=11 and 5 Hz), 4.17 (1H, br s), 4.69–4.88 (1H, m), 4.97 (1H, dd, J=10 and 4 Hz)

FABMS (+KI) m/z: 629 (MK$^+$)

EXAMPLE 7

(Synthesis of a compound of Formula(I) of the present invention wherein the group easily hydrolyzable to a hydroxyl group is a succinyloxy group)

Synthesis of Compound (26a) (R is an isobutyl group, A and X are each a succinyloxy group, and Y is a hydrogen atom)

0.062 g of Compound (19a) was dissolved in 1.0 ml of pyridine, and then 0.074 g of succinic anhydride and 0.038 g of 4-dimethylaminopyridine were added thereto, and the mixture was stirred at room temperature for 16 hours. The reaction solution, after addition of ethyl acetate, was successively washed with 5% hydrochloric acid and a saturated aqueous sodium chloride solution and dried over anhydrous magnesium sulfate. After evaporation of the solvent, the resulting residue was purified by silica gel column chromatography eluting with chloroform:methanol:acetic acid=25:1:catalytic amount (v/v) to give 0.062 g (yield: 68%) of a colorless amorphous product (26a).

IR (KBr) cm$^{-1}$: 2956, 1736, 1715, 1166

$^1$H-NMR (CDCl$_3$) δ (ppm):

0.67 (3H, s), 0.83 (3H, s), 0.89 (3H, d, J=6 Hz), 0.94 (3H, d, J=6 Hz), 2.50–2.75 (8H, m), 2.78 (1H, d, J=4 Hz), 3.09 (1H, d, J=4 Hz), 3.38 (1H, dd, J=11 and 5 Hz), 4.63–4.83 (1H, m), 4.91 (1H, dd, J=10 and 3 Hz)

FABMS (+KI) m/z: 659 (MK$^+$)

Utility of the present invention is illustrated by the following experiment.

Experiment: Growth Inhibition Action on KB cell (in vitro)

1) Test Method

1×10³ of KB cells/0.1 ml of a cell suspension in MEM medium containing 10% fetal bovine serum was placed in each well of a plate with 96 flat bottom wells, and incubated for 24 hours. This was dissolved in dimethylsulfoxide, and 100 µl of a solution (final concentration of dimethylsulfoxide: 0.5%) of a test compound diluted with the medium was added thereto, followed by incubation for 72 hours. After incubation, 4,5-dimethylthiazol-2-yl-2,5-diphenyltetrazolium bromide reagent (a color reagent) was added, and the mixture was further incubated for 4 hours.

100 µl of the medium (final concentration of dimethylsulfoxide:0.5%) was added as a control, and incubated in a similar manner. After incubation, the medium was removed, and the cells were dissolved in 150 µl of dimethylsulfoxide and the absorbance was determined. The ratio of the absorbance of the group treated with the test compound to that of the control group was determined, and the concentration of 50% growth inhibition ($IC_{50}$) was calculated.

2) Test Results $IC_{50}$ values of the test compounds [Compound (12a) and Compound A] on KB cells are shown in Table 1.

TABLE 1

| Test compound | $IC_{50}$ (µg/ml) |
| --- | --- |
| Compound (12a) | 0.0965 |
| Compound A | 0.0899 |

Industrial Applicability

According to the present invention, the novel steroid derivatives having the side chain at the 17-position which is simplified in structure (reduction of the number of asymmetric carbon atoms) were efficiently and stereoselectively provided by means of synthetic organic chemistry in place of Compound A which is an originally natural compound in ocean and therefore has a problem of maintaining the resource. The novel steroid derivatives of the present invention have a growth inhibiting action on KB cell comparable to Compound A, and can be easily prepared by means of synthetic organic chemistry, therefore they are useful as medicines having an antitumor action.

We claim:

1. A steroid derivative represented by the formula:

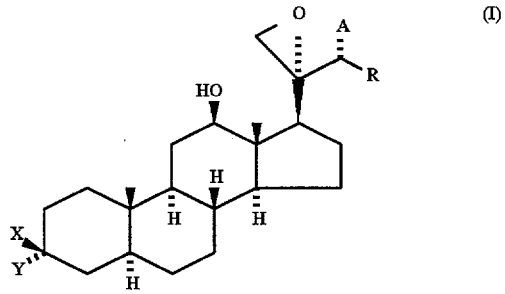

wherein R is a straight or branched alkyl group having 1 to 13 carbon atoms, A is a hydroxyl group or a group easily hydrolyzable to a hydroxyl group, with the caveat that R and A do not include asymmetric carbon atoms, X and Y together form an oxo group or an alkylenedioxy group having 2 or 3 carbon atoms, X is a hydroxyl group, an alkoxy group having 1 to 5 carbon atoms or a group easily hydrolyzable to a hydroxyl group, Y is a hydrogen atom or an alkoxy group having 1 to 5 carbon atoms, with the proviso that when X is a hydroxyl group or a group easily hydrolyzable to a hydroxyl group, Y is a hydrogen atom, and when X is an alkoxy group having 1 to 5 carbon atoms, Y is an alkoxy group having 1 to 5 carbon atoms, or salt thereof.

2. The steroid derivative according to claim 1 wherein the alkyl group is an isobutyl group, an isopentyl group, an isohexyl group, an isoheptyl group or an isooctyl group, or a salt thereof.

3. An antitumor agent comprising as an effective ingredient asteroid derivative or a salt thereof according to claim 1.

4. A method of treating tumors comprising the steps of inhibiting growth of KB cells by administering a pharmaceutically effective amount of a steroid derivative or a salt thereof according to claim 1 to a patient.

* * * * *